United States Patent [19]

Bhattacharjee

[11] Patent Number: 4,786,247
[45] Date of Patent: Nov. 22, 1988

[54] METHOD OF LENGTHENING THE FLAME FROM A GAS BURNER

[75] Inventor: Amal C. Bhattacharjee, Jackson Heights, N.Y.

[73] Assignee: Nabisco Brands, Inc., Parsippany, N.J.

[21] Appl. No.: 881,342

[22] Filed: Jul. 2, 1986

Related U.S. Application Data

[62] Division of Ser. No. 724,533, Apr. 18, 1985, Pat. No. 4,615,895.

[51] Int. Cl.[4] ............................................. F23C 5/14
[52] U.S. Cl. ......................................... 431/8; 431/252; 239/423
[58] Field of Search ............... 99/386, 443; 239/423, 239/543; 126/19 R, 91 A; 431/8, 252

[56] References Cited

U.S. PATENT DOCUMENTS

| | | | |
|---|---|---|---|
| 596,578 | 1/1898 | Dolan | 239/423 |
| 1,185,967 | 6/1916 | Beaver | 431/252 |
| 1,213,675 | 1/1917 | Maynard | 239/423 |
| 1,400,024 | 12/1921 | Caracristi | 239/423 |
| 1,702,625 | 10/1926 | Anderson et al. | 239/423 |
| 2,398,884 | 4/1946 | Crowe | 239/423 |
| 2,418,533 | 4/1947 | Walker | 239/422 |
| 2,638,159 | 11/1948 | Winkelman et al. | 239/423 |
| 2,641,313 | 6/1953 | Crossman | 431/329 |
| 2,911,035 | 12/1956 | Nieman et al. | 239/549 |
| 3,199,789 | 8/1965 | James | 239/423 |
| 3,340,794 | 9/1967 | Guiliano | 99/443 C |
| 3,360,029 | 9/1967 | Thompson | 431/329 X |
| 3,418,062 | 8/1966 | Hovis et al. | 431/350 |
| 3,706,520 | 12/1972 | Grimm et al. | 431/10 |
| 3,850,571 | 11/1974 | Zink et al. | 431/349 |

FOREIGN PATENT DOCUMENTS

| | | | |
|---|---|---|---|
| 321441 | 3/1975 | Austria . | |
| 742915 | 7/1944 | Fed. Rep. of Germany | 99/443 C |
| 2350846 | 10/1973 | Fed. Rep. of Germany . | |
| 595945 | 10/1925 | France | 99/443 C |
| 598960 | 10/1959 | Italy | 99/443 C |
| 185924 | 9/1922 | United Kingdom | 99/443 C |

Primary Examiner—Samuel Scott
Assistant Examiner—Allen J. Flanigan
Attorney, Agent, or Firm—Richard Kornutik

[57] ABSTRACT

A ribbon gas burner for use in a baking oven has a row of gas apertures disposed between two rows of air apertures through which air is forced under pressure. The streams of air issuing from the two rows of air apertures are inclined inwardly towards the gas stream, thereby lengthening the ribbon flame produced by the burner and improving the uniformity of heating within the band oven.

1 Claim, 3 Drawing Sheets

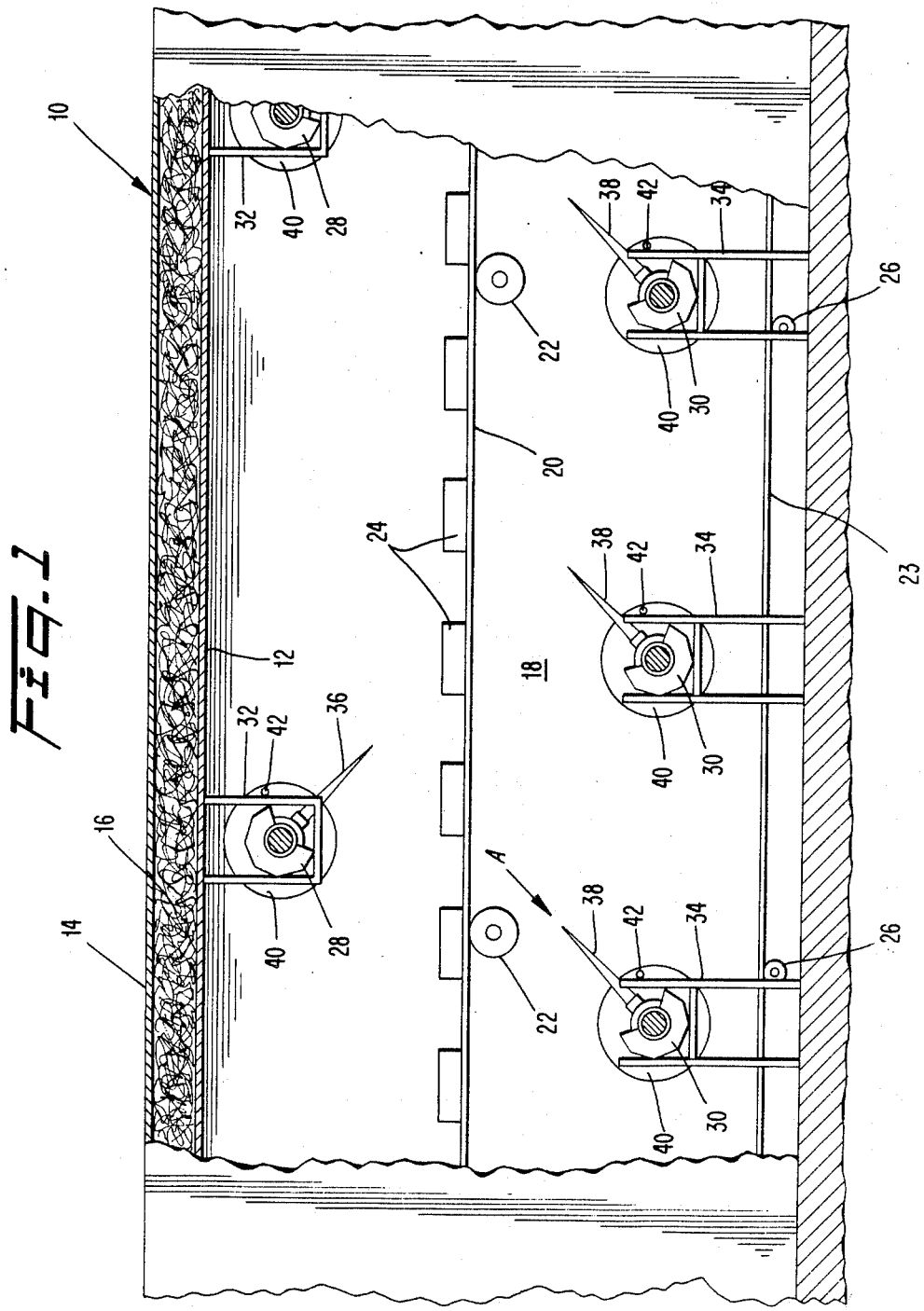

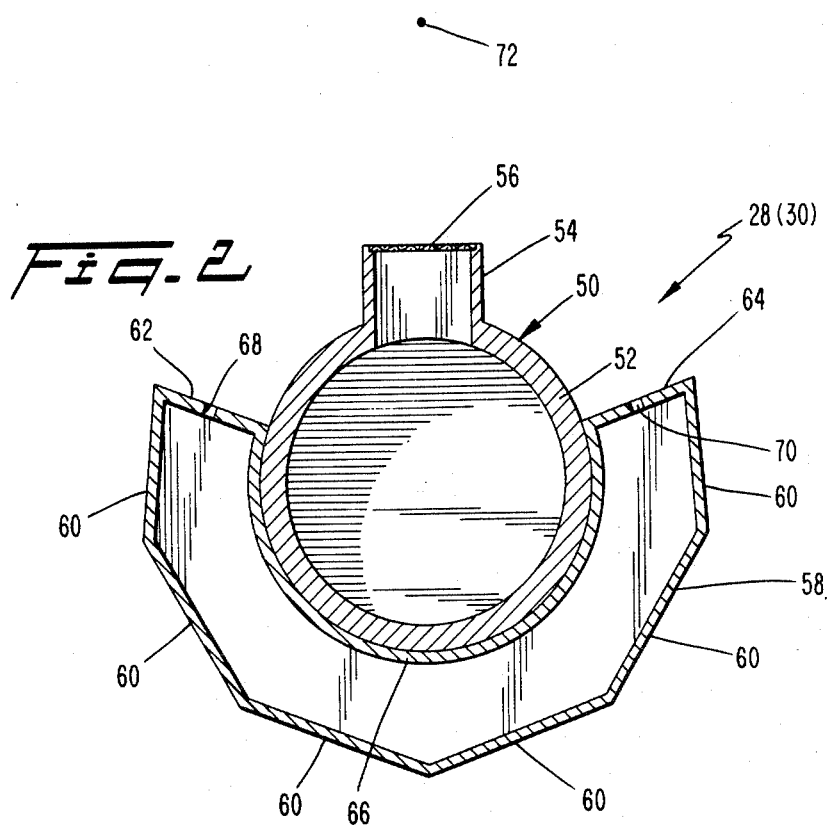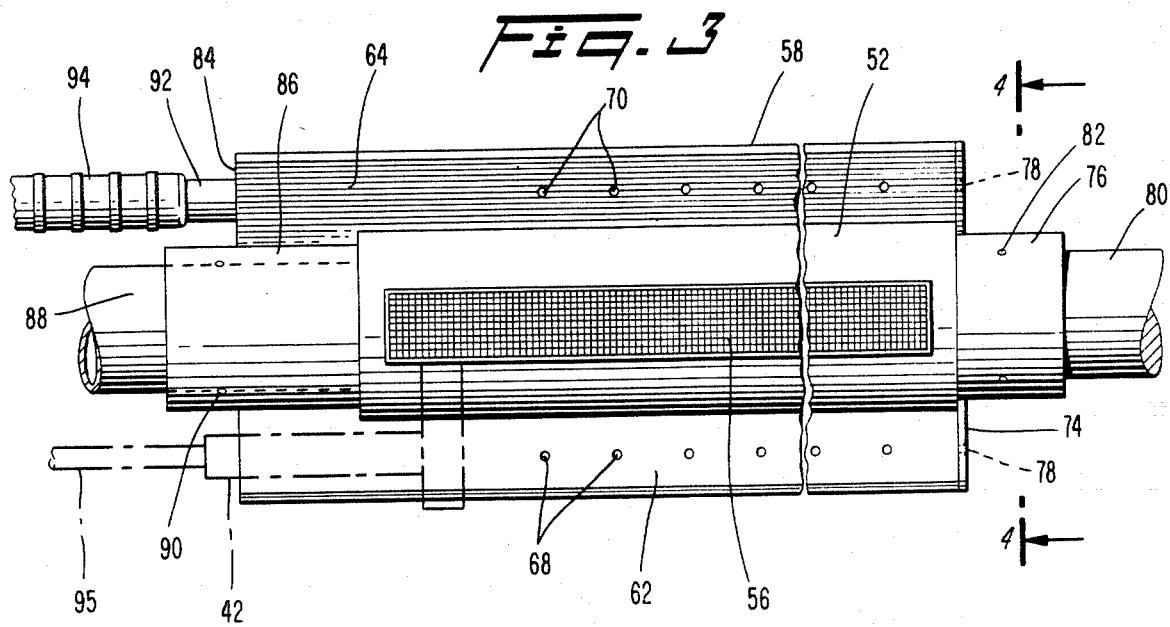

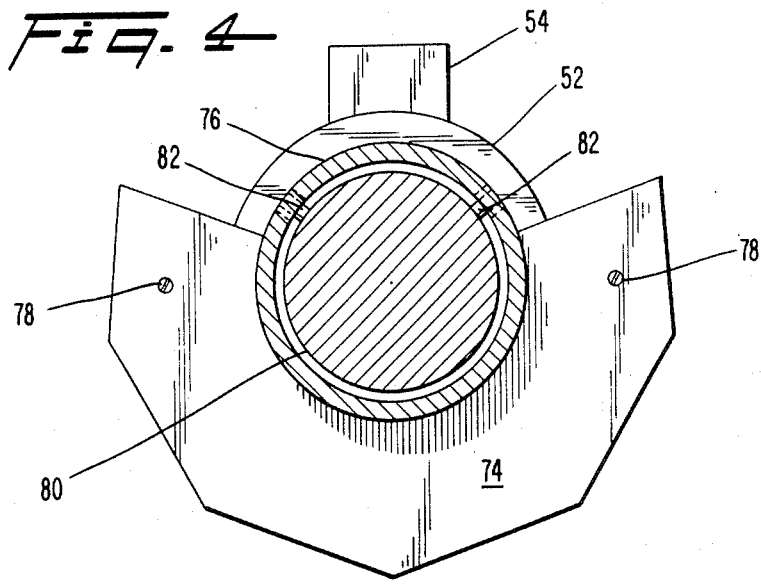
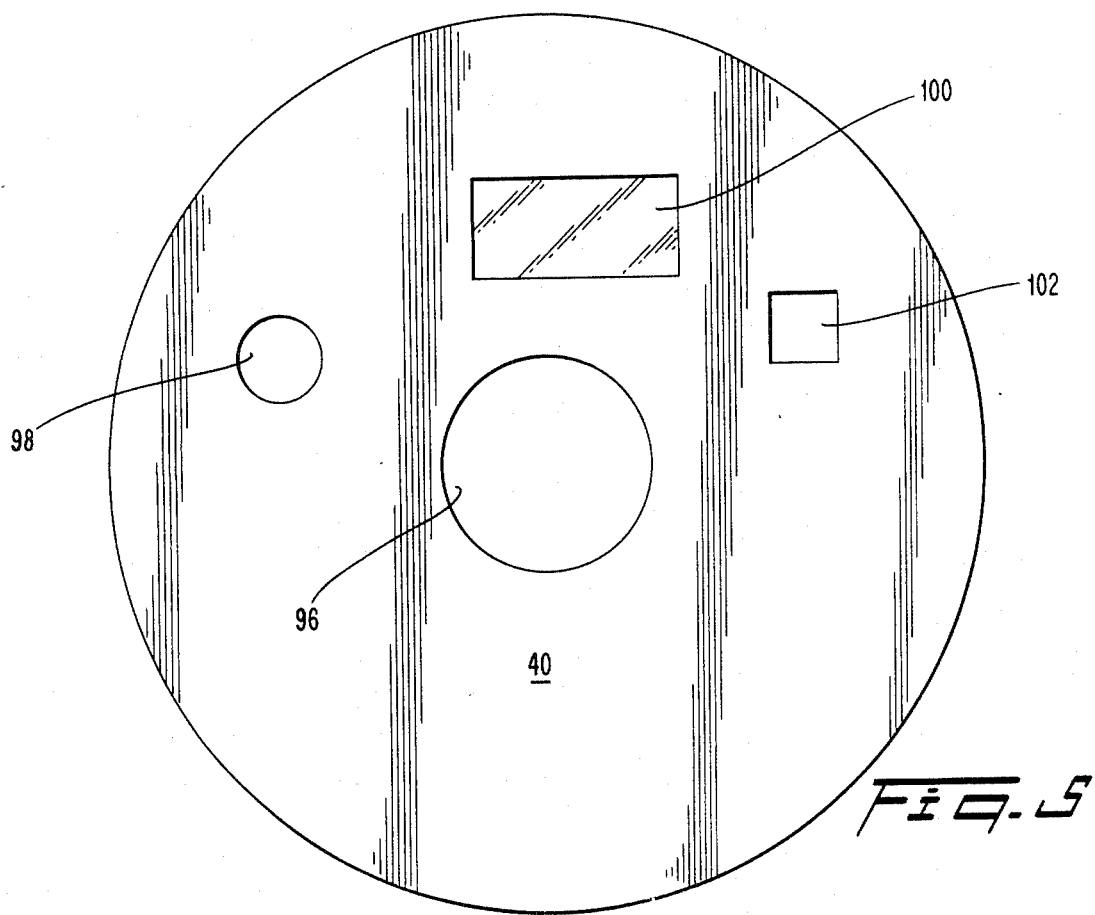

METHOD OF LENGTHENING THE FLAME FROM A GAS BURNER

This is a division of application Ser. No. 724,553, filed Apr. 18, 1985 now U.S. Pat. No. 4,615,895.

FIELD OF THE INVENTION

This invention relates to a forced air/gas burner and a baking oven incorporating such a burner. The invention also provides a process for baking dough goods using such an oven.

BACKGROUND OF THE INVENTION

In high-volume production of baked goods, for example cookies, crackers, bread, rolls etc., baking of the goods is conventionally effected using a band oven. Such a band oven comprises an insulated housing enclosing a baking chamber of considerable length; chambers in commercial ovens are typically around 300 feet (approximately 90 meters) long. A belt conveyor formed of a heat-resistant material, typically steel mesh, extends longitudinally through the baking chamber and extends beyond both ends of the baking chamber. Goods to be baked are placed on the inlet end of the belt conveyor, which moves continuously and thus carries a continuous stream of goods through the baking chamber. The speed of the conveyor is regulated so that the goods being baked remain within the baking chamber for the proper baking time, and the baked goods are continuously discharged from the outlet end of the conveyor.

Heating of the baking chamber is conventionally effected by means of elongate gas burners which extend transversely across the conveyor at spaced intervals, each of these gas burners being provided with a row of apertures through which gas issues to form either a large number of individual flames lying close to one another, or a single continuous ribbon-like flame extending the full length of the row of apertures. Either form of flame will hereinafter be referred to as a "ribbon flame". To render supervision and maintenance of the band oven as simple as possible, one side of the housing is provided with a series of removable plates, one adjacent the end of each gas burner, these removable plates each bearing a gas supply aperture through which gas is supplied to the burner and a transparent window through which an operator can observe the gas burner to ensure that proper combustion is taking place. The plate may also be provided with an inlet for power connections to an igniter placed adjacent the gas burner to ignite the gas issuing from the burner.

A major consideration in the operation of such band ovens is to ensure uniformity of heating along the band, since if non-uniform distribution of heat occurs, with the development of hot zones on the band adjacent each burner and cooler spots midway between adjacent burners, the baking of the goods may be deleteriously affected, and excessive gas consumption may occur. (References to non-uniformity of heating herein refer to such non-uniformity of heating over the relatively short distances between adjacent gas burners and are not intended to refer to deliberate creation of zones of differing temperature along the length of the band oven which are often deliberately introduced, for example to ensure that the goods entering the oven are rapidly raised to a proper baking temperature.) Non-uniformity of heating can be reduced by using a large number of burners spaced apart by relatively small distances. For example, in prior art band ovens burners may be spaced at intervals of 12 to 18 inches (305 to 457 mm.) along the length of the band, the burners being disposed in two rows above and below the band.

Unfortunately, when such a large number of burners are employed the rate at which gas needs to be burned at each burner to maintain the requisite baking temperature within the insulated baking chamber is low, so that only a short flame is produced at each burner, and the burner thus provides a concentrated heat source, thereby tending to produce non-uniformity of heating within the baking chamber. Thus, improvement in the uniformity of heating within band ovens is desirable.

U.S. Pat. No. 596,578 describes an acetylene burner in which gas is forced under pressure through a duct into a slot where it comes into contact with air contained within the slot and contacts a flat vertical wall of the slot opposite the side to which the gas enters so that the column of gas is flattened. This flattened column of gas, following upwardly along the vertical face of the wall of the slot, passes out of the slot, where it is ignited and a flat, uniform and smokeless blaze is produced.

U.S. Pat. No. 1,213,675 to Maynard describes an oil burner having a slot-like aperture through which the oil is discharged, and a steam conduit through which steam passes into a large number of apertures, which emerge from the burner adjacent the slot-like oil aperture, so that the steam is projected from the burner in a substantially fan-shaped form contacting and mixing with oil projected through the oil conduit to atomize the oil.

U.S. Pat. No. 1,400,024 to Caracristi describes a gas burner in which control of the gas/air ratio is effected by providing an air supply conduit, which is separate from the gas supply conduit, and through which air is forced under pressure. The combustible gas emerges from the burner through a set of slot-like gas apertures arranged parallel to one another, while the air emerges through a set of slot-like air apertures disposed between adjacent pairs of the gas apertures, so that parallel alternating flat streams of gas and air emerge from the burner. It is stated that the alternate layers of gas and air emerging from the slotted outlets form a stratified stream at the exit, the gas and air then becoming thoroughly intermixed so that the regulation of the air both as to velocity, pressure and volume enables a proper quantity of air to be provided depending upon the quality of the gas, thus providing maximum combustion effeciency.

U.S. Pat. No. 1,702,625 to Anderson et al. describes a gas burner having the form of an elongate trapezoidal prism. This prism is hollow, having an internal trapezoidal chamber open at both top and bottom, flanked by two almost triangular prismatic gas chambers closed at their lower ends but having narrow, slot-like apertures at their upper ends. The jets of combustible gas emerging from the upper ends of these two gas chambers are angled inwardly towards one another so that they meet along a line lying above the central chamber of the gas burner. This arrangement allows air to be drawn up through the central chamber of the gas burner, thereby augmenting the air supply along the line at which the gas jets meet and, so the patent states, producing an intensely hot flame tip along this line.

U.S. Pat. No. 2,418,533 to Walker describes a gas torch designed so that it is capable of being operated very hot with no possibility of flashbacks and so that high velocity and highly oxidizing flame jets can be employed without danger of the flames blowing away from the tip or blowing out. This gas torch has a tip of elongate rectangular form having a slot of rectangular cross-section extending longitudinally therein. Combustible gas is supplied to two gas conduits each of which communicates with the base of the slot via a row of apertures, the two rows of apertures being on opposed sides of the slot. Oxygen is supplied through a third conduit from which extend a row of branch conduits, this row of branch conduits running parallel to the length of the slot. However, the oxygen branch conduits do not open into the slot, as do the gas conduits, but instead terminate in nozzles which extend upwardly along the central plane of symmetry of the slot and terminate flush with the outer surface of the slot.

U.S. Pat. No. 2,638,159 to Winkleman et al. describes a gas burner intended for producing very high temperatures for use in stripping coatings such as rust, scale, paint and other organic coatings from the surfaces of wood, metal and other bodies. In this burner, combustible gas emerges from a single row of apertures. Oxidizing gas is supplied via two rows of apertures, parallel to each other and to the row of apertures for the combustible gas, both rows of oxidizing gas apertures lying on the same side as the combustible gas apertures. The two sets of conduits which terminate in the two rows of oxidizing gas apertures are angled both with respect to each other and with respect to the set of conduits which terminate in the combustible gas apertures, so that the stream of combustible gas and the two streams of oxidizing gas intersect along a single line. This retards the velocity at which the oxidizing gas is supplied to the surface coating to be treated, and thus causes the oxidation action of the burner to be uniform over the width covered by the burner, rather than concentrated in narrow paths corresponding to separate jets of oxidizing gas.

U.S. Pat. No. 2,911,035 to Nieman et al. describes a gas burner for producing a soft, silent flame of extremely high temperature. In this burner, a single casing is provided with a large number of apertures, some being connected to the combustible gas supply and the remainder to the oxygen supply, the oxygen and combustible gas apertures being intimately mixed together so that mixing of oxygen and combustible gas takes place only after the gases have left the burner, thereby preventing flashback. However, the oxygen and combustible gas apertures are so close together that intimate mixing takes place almost at once and complete burning takes place with a very short distance from the plate.

U.S. Pat. No. 3,418,062 to Hovis et al. describes a substantially cylindrical burner intended for use in a soaking pit. In this burner, a central fluid fuel outlet is surrounded by two concentric rings of combustion air outlets. The fuel outlet and the inner ring of gas outlets direct fuel and air respectively parallel to the axis of the burner, while the outer ring of gas outlets projects jets of air diverging away from the axis of the burner.

U.S. Pat. No. 3,706,520 to Grimm et al. describes a complicated fuel gas burner for a vertical shaft furnace. This burner includes a single shaft containing four concentric conduits, the conduits containing fuel, air, fuel and air respectively reading from the innermost conduit. The three inner conduits terminate in separate plena each provided with a plurality of outlets arranged to direct the fuel or air substantially perpendicular to the axis of the shaft. The outermost conduit opens into a jacket which directs the air backwards in the opposite direction to the main fuel and air flow, so that the outermost air is directed backwards parallel to the axis of the shaft.

U.S. Pat. No. 3,850,571 to Zink et al. describes a high energy flame burner intended to produce a long, slender, rod-jet of flame of small diameter. The flame burner has a substantially cylindrical tube the tip of which is provided with a principal gas outlet orifice through which a combustible gas jet flows axially of the burner. In the side walls of the burner are cut a plurality of secondary gas outlets, which issue into a collar surrounding the burner. The forward end of this collar is provided with a forwardly-diverging frusto-conical flange, while the rear wall of the collar is provided with a plurality of apertures. The flow of combustible gas through the secondary gas apertures draws air through the apertures in the rear wall of the collar and the resultant mixture of gas and air is caused by the frusto-conical flange to issue from the forward end of the collar as an outwardly diverging ring of flame encasing the principal gas jet so as to assist in the ignition of the gas in the principal jet, and prevent it from being blown out due to the high velocity of the jet.

None of the above patents indicate any way in which the ribbon gas jet from a gas burner used in a band oven could be modified so as to improve the uniformity of heating within the band oven, and there is thus still a need for a solution to the problem of non-uniformity of heat distribution in band ovens. The present invention provides a way of improving the uniformity of heat distribution in a band oven.

SUMMARY OF THE INVENTION

This invention provides a baking oven comprising a housing having walls defining a chamber, transport means for moving articles to be baked through the chamber, and a plurality of gas burners mounted within the chamber and spaced from one another. At least one of these gas burners comprises a gas supply conduit, and an elongate gas plenum communicating with the gas supply conduit, the gas plenum having walls defining a row of apertures spaced from one another along the length of the gas plenum and extending from the interior of the gas plenum to the external surface thereof, such that gas issuing from these apertures will burn to produce a flame extending along the length of the gas plenum. The burner or burners further comprises an air supply conduit and at least one air plenum communicating with the air supply conduit, this air plenum or plena having walls defining two row of apertures extending from the interior of the air plenum or plena to the external surface thereof, the two rows of apertures being disposed on opposed sides of the rows of apertures in the gas plenum and being directed towards the row of apertures in the gas plenum such that air issuing from the two rows in the air plenum will impinge upon the flame produced by the gas issuing from the row of apertures in the air plenum and lengthen the flame.

This invention also provides a process for baking dough goods, this process comprising transporting the dough goods through a baking oven provided with a plurality of gas burners each having walls defining a row of gas apertures, supplying gas to the burners, whereby a stream of gas passes through the gas apertures and burns adjacent the gas burner, and, in at least one of the gas burners, directing two streams of air from opposed sides of the flame produced by the burning gas inwardly towards the flame, each stream of air being directed at an acute angle to the direction of the gas issuing from the gas apertures, thereby causing the streams of air to impinge upon and lengthen the flame.

This invention also provides a method of lengthening the flame from a gas burner which produces an elongate flame, the method comprising directing two streams of air from opposed sides of the flame inwardly towards the flame, each stream of air being directed at an acute angle to the direction of the gas issuing from the gas burner, thereby causing the streams of air to impinge upon and lengthen the flame.

Finally, this invention provides a gas burner for producing a ribbon flame, the gas burner comprising an elongate gas plenum having a row of gas apertures through which gas can issue and burn to produce a ribbon flame, and at least one air plenum having walls defining two rows of air apertures disposed on opposed sides of the row of gas apertures, the two rows of air apertures being arranged to produce two streams of air inclined inwardly toward the gas issuing from the row of gas apertures with the streams of air being directed at acute angles to the stream of gas.

BRIEF DESCRIPTION OF THE DRAWINGS

FIG. 1 is a side elevation of part of a band oven of the invention with part of the housing broken away to show the arrangement of the band, the gas burners, and associated parts of the oven;

FIG. 2 is a vertical section through one of the gas burners shown in FIG. 1, this section being taken in a plane parallel to FIG. 1 and perpendicular to the long axis of the burner;

FIG. 3 is a plan view of the burner shown in FIG. 2 looking in the direction of arrow A in FIG. 1;

FIG. 4 is a section along the line 4—4 in FIG. 3; and

FIG. 5 is a side elevation of the removable plate in the wall of the band oven associated with the burner shown in FIGS. 2, 3 and 4.

DETAILED DESCRIPTION OF THE DRAWINGS

The baking oven (generally designated 10) shown in FIG. 1 comprises a housing having, at its top and sides, an inner wall 12, an outer wall 14 and a layer of insulation 16 formed of, for example, fiberglass disposed between the inner and outer walls. The housing will typically be about 300 feet (90 meters) long, and only a small portion of the housing is shown in FIG. 1.

The housing encloses an elongate cuboidal baking chamber 18 along the length of which runs a belt conveyor formed of a heat-resistant material, for example steel wire mesh. The upper land 20 of the belt conveyor is supported at intervals by idler rollers 22 and lies in a horizontal plane approximately half-way up the baking chamber 18. The upper land 20 of the belt conveyor transports dough goods 24 being baked (from left to right in FIG. 1) longitudinally through the baking chamber 18, the speed of movement of the conveyor and the temperatures within the chamber 18 being adjusted so that the goods 24 are properly baked as they pass through the oven. The lower land of the belt conveyor runs longitudinally through the baking oven adjacent the bottom of the chamber 18 and is supported by idler rollers 26. Although for purposes of illustration the spacing between the rollers 26 has been made the same as that between the rollers 22 in FIG. 1, in practice the spacing between the idler rollers 26, which support the non-load bearing lower land of the conveyor, can usually be greater than the space in between the rollers 22, which must support the upper land 20 of the conveyor and the goods 24 resting thereon.

Although not shown in FIG. 1, the belt conveyor projects from both ends of the baking chamber 18 (the ends of the housing are of course provided with appropriate apertures to allow entry and exit of the conveyor) and the belt conveyor is powered by driven rollers at either end. The baking oven is also provided with conventional exhaust ducts, fans and fan motors, these parts being omitted from FIG. 1 for ease of illustration.

The baking chamber 18 is heated by a large number of gas burners (generally designated 28 and 30). The gas burners 28 and 30 are of elongate, substantially prismatic form and are arranged with their long axes horizontal and extending transversely across the baking chamber 18, these axes lying parallel to the horizontal surface of the upper land 20 of the conveyor but perpendicular to the direction of movement thereof. The gas burners are arranged in two rows above and below the upper land 20 of the conveyor, the burners 28 in the upper row may be spaced at intervals of about 3 to 4 feet (0.91 to 1.22 m.) while the burners 30 in the lower row may be spaced at intervals of about 18 to 24 inches (457 to 609 mm.). The burners 28 in the upper row are supported by U-shaped hangers 32 fixed to the top of the inner wall 12, while the burners 30 in the lower row are supported by substantially H-shaped supports 34 resting on the base of the oven. Although not apparent from FIG. 1, the hangers 32 and supports 34 do not extend the full width of the oven; instead, each hanger of support has a width of only about 1 inch (25 mm.), two separate hangers or supports being provided for each burner 28 or 30, one adjacent each end of the burner.

Each of the burners 28 or 30 produces a flat ribbon flame 36 or 38 respectively, these flames extending the full width of the upper land 20 of the conveyor. The flames 36 from the upper burners 28 are directed downwardly toward the upper land 20 and down the direction of the movement of this land. Similarly, the flames 38 from the lower burners 30 are directed upwardly towards the upper land 20 and down the direction of movement of this land.

For ease of operation, supervision and maintenance, the baking oven 10 is arranged so that all the gas supply conduits and other connections are arranged in one side wall of the housing, this side wall being designated the "operating side" of the oven. The oven is viewed in FIG. 1 from its non-operating side. To provide the necessary gas and other connections to each burner, a removable plate 40 is provided in the side wall of the housing on the operating side of the oven. In addition to the gas supply, the removable plate carries power connections to an electric igniter 42 disposed adjacent each burner.

The construction of the burner is shown in more detail in FIGS. 2 and 3. Although as noted above, the burners 28 and 30 are arranged so that their flames 36 and 38 are directed transversely downwardly or transversely upwardly respectively within the baking chamber 18, for ease of reference in FIGS. 2 and 3 the burner has been shown and will be described as though it produced a flame directed vertically upwardly.

As best seen in FIG. 2, the burner 28 or 30 comprises a gas plenum (generally designated 50) having the form of an elongate hollow tube 52 bearing on its uppermost part a substantially cuboidal extension 54. The upper surface of the extension 54 is formed by a strip of steel mesh 56 running along the length of the tube 52. The apertures in the mesh strip 56 constitute the row of gas apertures of the burner. It will be apparent to those skilled in the art of burner technology that gas issuing from the apertures in the mesh strip 56 and burning adjacent these apertures will provide a continuous ribbon flame extending the full length of the mesh strip 56.

The burner 28 or 30 further comprises an air plenum 58. The air plenum 58 has six flat faces 60, which form four complete sidewalls, and part of two further sidewalls of a regular nonagonal prism, two further flat faces 62 and 64 which lie in planes including the superimposed axes of the tube 52 and the nonagonal prism and at an angle of 140° to one another, and a part-cylindrical section 66 which extends in contact with and surrounding the tube 52 over the 220° sector of the tube between the faces 62 and 64.

As best seen in FIG. 3, the two surfaces 62 and 64 each have provided therein a row of air apertures 68 and 70 respectively. These air apertures 68 and 70 are the outlets of air conduits which are drilled normally through the surfaces 62 and 64 into the hollow interior of the air plenum 58. Because of the 140° angle between the surfaces 62 and 64, and the symmetrical disposition of these surfaces about the extension 54 of the gas plenum 50, when jets of air (produced as explained below) emerge from the apertures in the surfaces 62 and 64 respectively, these jets of air converge inwardly towards a jet of gas (also produced as described below) emerging from the apertures in the mesh strip 56, so that the gas and air jets meet along a single line 72 (FIG. 2). The convergence of the air jets from either side on to the flame produced by the burning gas increases the length of the flame, thereby improving the uniformity of heating of the baked goods on the upper land 20 of the belt conveyor (FIG. 1). By proper adjustment of the pressures of the gas and air fed to the gas and air plena 50 and 58 respectively (such adjustment being easily effected empirically by routine methods) the air streams allow very marked elongation of the flame. For example, it has been found that using a gas pressure of 6 psig gauge (41.5 kPa.), and air apertures 0.125 inch (3.2 mm.) in diameter and spaced at 1 inch (25 mm.) intervals along the surfaces 60 and 62, with an air pressure of 16 inches water gauge (4 kPa.) results in a flame approximately 6 inches (152 mm.) long, as compared to a flame approximately 1½ inches (38 mm.) long when no air supply is used.

As shown in FIG. 3, at the end of the burner which lies adjacent the non-operating side wall of the oven (the right-hand end in FIG. 3) the air plenum is closed by a flat endplate 74. As best seen in FIG. 4, this endplate 74 has a form corresponding to the cross-section of the air plenum 58 except that it is provided with an axial cut-out surrounded by a collar 76, which is integral with the endplate 74, the endplate 74 is secured to the body of the air plenum 58 by set screws 78. A blind nipple 80 extends axially from the adjacent end of the tube 52 and passes through the collar 76. The collar 76, and thus the gas plenum 58, is fixed in position relative to the tube 52 by set screws 82.

At the left-hand end (in FIG. 3) of the burner, which lies adjacent the operating side wall of the oven, the air plenum extends axially beyond the end of the tube 52 to an endplate 84, which is integral with the side walls 60, 62 and 64 of the air plenum 58. The endplate 84 carries an integral collar 86. Unlike the collar 76 already described, the collar 86 extends axially both inwardly and outwardly from the endplate 84; the part-cylindrical recess in the air plenum provided by the section 66 terminates short of the endplate 84 so that the hollow interior of the collar 86 in effect forms a reduced-diameter continuation of this recess.

A gas supply tube 88 extends axially from the tube 52 and passes through the collar 86, which is clamped to the gas supply tube 88 by set screws 90. The gas supply tube 88 communicates with the interior of the tube 52 of the gas plenum and supplies combustible gas thereto.

The endplate 84 of the air plenum 58 also has an aperture provided therein, but in this case the aperture is spaced from the axis of the gas plenum and lies adjacent one of the side walls of the air plenum. The aperture in the endplate 84 is surrounded by a cylindrical stub tube 92, which is connected to a flexible metal tube 94, through which air is supplied under pressure to the air plenum. The electric igniter 42 is provided at this end of the burner, but in order to show the construction of the burner at this end of the burner more clearly, the igniter 42, which serves to ignite gas issuing from the burner and which is of a conventional type, and its associated power connections 95 are indicated only schematically in broken lines in FIG. 3.

FIG. 5 shows the removable plate 40 disposed in the operating side wall of the oven adjacent each burner 28 or 30. The plate 40 is circular and covers a somewhat smaller circular aperture in the operating side wall of the oven, being releasably secured to the side wall by screws. The plate 40 has a central gas inlet aperture 96, through which passes a tube which is secured to the gas supply tube 88 shown in FIG. 3. The plate 40 is also provided with an off-center air inlet aperture 98 through which passes a tube which is secured to the flexible metal tube 94 connected to the air plenum 58. The use of the flexible metal tube 94 enables the same plate 40 to be used for both the upper and lower rows of burners 28 and 30 respectively (FIG. 1) despite the difference in the positions of the stub tube 92 because of the different orientations of the two rows of burners. A transparent window 100 is formed in the upper part of the plate 40; this window is of course formed of a material resistant to the temperatures to which it will be exposed by virtue of its proximity to the flame issuing from the burner. The window 100 is provided to enable an operator to check that a proper flame is being produced by the burner. Finally, the plate 40 is provided with an igniter power inlet 102 through which pass wires connected to the power connections 95 of the igniter 42.

As will be apparent to those skilled in the art, the tubes passing through the apertures 96 and 98 in the plate 40 are connected to conventional gas and compressed air lines via appropriate pressure-reduction or metering valves in order to ensure that air and gas are supplied to the burner at the proper pressures, while the power connections to the igniter 42 are connected to an appropriate power supply via a conventional switch.

To assemble the burners 28 and 30 the blind nipple 80 and the gas supply tube 88 are first inserted into their respective apertures in the gas plenum 50; although not shown in the drawings the appropriate ends of the nipple 80 and the tube 88, and the apertures into which they fit, are provided with cooperating screw threads. Apart from the separate nipple 80 and tube 88, the gas plenum 50 is a single, integral casting.

The air plenum 58, with its endplate 74 and associated collar 76 removed, has its part-cylindrical section 66 engaged with the left-hand end (in FIG. 3) of the tube 52, and is slid along the tube 52, from left to right in FIG. 3 until the end of the tube 52 carrying the gas supply tube 88 abuts the shoulder where the part cylindrical section 66 meets the collar 86. The endplate 74 and its associated collar 76 are slid over the nipple 80 to their correct positions relative to the air plenum 58, fastened to the air plenum by means of the set screws 78 and finally clamped to the nipple 80 by means of the set screws 82. Finally, the set screws 90 are inserted to clamp the collar 86 to the tube 88. The nipple 80 and the tube 88 can then be placed on the hangers 32 or supports 34 and the gas and air supplies connected.

It will be seen that, if either the gas plenum or the air plenum of the burner has to be replaced because of, for example, wear or mechanical failure, either plenum can be replaced without the other, simply by disassembling the burner in precisely the reverse of the assembly operation described above.

From the foregoing description of the preferred burner shown in the accompanying drawings, it will be apparent that the construction of this burner allows for easy retrofitting of existing band ovens provided with conventional burners. Most conventional burners closely resemble the gas plenum 50 of the preferred burner of the present invention, and hangers and supporters suitable for supporting such a conventional burner can also be used with the preferred burner of the present invention, since the rod 74 and the gas supply tube 80 of the burner of the present invention can have dimensions identical to the corresponding parts of a conventional burner. Moreover, existing burners can be modified simply by sliding a gas plenum over the burner, as already described. It will of course be necessary to modify conventional plates corresponding to the plate 40 shown in FIG. 5 to provide for a pressurized air inlet, but in many cases it may be possible to re-use plates already provided with a gas inlet aperture, window and igniter power inlet simply by boring or otherwise cutting an appropriate aperture 98 in the plate. The use of the flexible metal tube 94 allows considerable latitude in the placing of the aperture 98 in the plate 40. The provision of the necessary compressed air line and appropriate branch lines involved to supply compressed air to the burners is well within the capacity of those skilled in the art, and does not involve any difficult design considerations, especially in view of the very low (and consequently safe) air pressures involved.

It will be apparent to those skilled in the art that numerous changes and modifications can be made in the preferred embodiment of the invention described above without departing from the scope of the invention. For example, the 20° angle between the gas and air streams in the preferred burner can be varied. In fact, almost an acute angle can be used over the range of both (say) 5° to 80°. However, a relatively small acute angle within the range of about 10° to about 30° is preferred, since it has been found that the use of an angle within this range gives maximum lengthening of the flame issuing from the burner. Since it is desirable to avoid deflecting the gas flame from the plane in which it would lie if no forced air streams were present, it is desirable that the acute angles between the two air streams and the gas stream be equal to one another.

The dimensions of the oven of the present invention and the burners therein can vary very widely, and the following suggestions are given solely by way of general guidance. If the housing of the oven is to be a typical commercial housing having a length of approximately 300 feet (90 meters), a height of approximately 5 feet (1.5 meters) and a belt conveyor having a width of 38 inches (965 mm.), it has been found appropriate to use a burner measuring 42½ inches (1079 mm.) between the endplates 74 and 84, with a gap of 1½ inches (38 mm.) between the endplates 84 and the adjacent end of the tube 52. In this burner, the surfaces 62 and 64 are each provided with 39 holes 0.125 inch (3.2 mm.) in diameter spaced at intervals of 1 inch (25 mm.) beginning 1 inch (25 mm.) from the endplate 74 and terminating 2 inches (51 mm.) short of the opposed end of the tube 52. The tube 52 is 1¾ inches (44 mm.) in internal diameter, with the mesh 56 spaced 1 15/16 inch (49 mm.) from the axis of the tube 52. With the air streams angled at 20° to the gas stream, as shown in the drawings, a burner of these dimensions has the line 72 of intersection of the air and gas streams spaced 5⅛ inches (130 mm.) from the axis of the tube 52. The air pressure used is desirably in the range of about 8 to about 32 inches water gauge (about 2 to about 8 kPa. gauge).

In view of the numerous possible changes and modifications in the oven, baking process and method of the present invention (these changes and modifications not being limited to those already discussed), the whole of the foregoing description is to be construed in an illustrative and not in a limitative sense, the scope of the invention being defined solely by the appended claims.

I claim:

1. A method of lengthening the flame from a gas burner which produces a substantially planar ribbon flame, the method comprising directing two streams of air symmetrically upon the flame from opposed sides thereof inwardly towards the flame, the two streams of air being directed at equal acute angles in the range of from about 10° to about 30° to the plane of the flame, thereby causing the streams of air to impinge upon and lengthen the flame.

* * * * *